United States Patent
Caduff et al.

(10) Patent No.: US 7,184,810 B2
(45) Date of Patent: Feb. 27, 2007

(54) METHOD AND A DEVICE FOR MEASURING GLUCOSE

(75) Inventors: Andreas Caduff, Zurich (CH); Yuri Feldman, Jerusalem (IL)

(73) Assignee: Solianis Holding AG, Zug (CH)

( * ) Notice: Subject to any disclaimer, the term of this patent is extended or adjusted under 35 U.S.C. 154(b) by 0 days.

(21) Appl. No.: 11/070,853

(22) Filed: Mar. 2, 2005

(65) Prior Publication Data

US 2005/0203361 A1    Sep. 15, 2005

Related U.S. Application Data

(63) Continuation of application No. PCT/IB02/03604, filed on Sep. 4, 2002.

(51) Int. Cl.
A61B 5/00    (2006.01)
A61B 5/05    (2006.01)

(52) U.S. Cl. ....................... 600/347; 600/365

(58) Field of Classification Search ............... None
See application file for complete search history.

(56) References Cited

U.S. PATENT DOCUMENTS

| | | |
|---|---|---|
| 4,509,531 A | 4/1985 | Ward |
| 4,679,426 A | 7/1987 | Fuller et al. |
| 4,765,179 A | 8/1988 | Fuller et al. |
| 4,875,486 A | 10/1989 | Rapoport et al. |
| 5,050,612 A | 9/1991 | Matsumura |
| 5,077,476 A | 12/1991 | Rosenthal |
| 5,109,855 A | 5/1992 | Gunter |
| 5,353,802 A | 10/1994 | Ollmar |
| 5,508,203 A * | 4/1996 | Fuller et al. ............ 436/149 |
| 5,771,891 A * | 6/1998 | Gozani ................. 600/347 |
| 5,792,668 A * | 8/1998 | Fuller et al. ............ 436/149 |
| 5,804,967 A | 9/1998 | Miller et al. |
| 5,890,489 A | 4/1999 | Elden |
| 6,028,433 A | 2/2000 | Cheiky-Zelina et al. |
| 6,182,504 B1 | 2/2001 | Gaisford |
| 6,309,884 B1 | 10/2001 | Cooper et al. |
| 6,320,393 B1 | 11/2001 | Yasui et al. |
| 6,356,776 B1 | 3/2002 | Berner et al. |
| 6,517,482 B1 * | 2/2003 | Elden et al. ............ 600/309 |
| 6,565,509 B1 | 5/2003 | Say et al. |
| 6,723,048 B2 * | 4/2004 | Fuller ................ 600/365 |

(Continued)

FOREIGN PATENT DOCUMENTS

AT    395 075    9/1992

(Continued)

OTHER PUBLICATIONS

English Abstract of AT 395 075 dated Sep. 10, 1992.

(Continued)

*Primary Examiner*—Robert L. Nasser
(74) *Attorney, Agent, or Firm*—Ladas & Parry LLP

(57) ABSTRACT

In order to measure the glucose level in the body tissue of a subject, a probe is applied the subject's skin. Electric pulses from a pulse generator are fed to the probe and partially reflected back to a measuring device, where a time resolved measurement is made. The charge obtained from an integration of the measured voltage is transformed to a glucose level using data from a calibration table. This method allows to monitor glucose non-invasively.

8 Claims, 3 Drawing Sheets

U.S. PATENT DOCUMENTS

| | | |
|---|---|---|
| 2002/0106709 A1 | 8/2002 | Potts et al. |
| 2002/0155615 A1 | 10/2002 | Novikov et al. |
| 2003/0153821 A1 | 8/2003 | Berner et al. |
| 2004/0104736 A1 | 6/2004 | Cohen et al. |
| 2004/0133353 A1 | 7/2004 | Geutebruck |
| 2004/0147819 A1 | 7/2004 | Caduff et al. |
| 2004/0240512 A1 | 12/2004 | Pesach |
| 2005/0101842 A1 | 5/2005 | Suda |
| 2005/0113662 A1 | 5/2005 | Kjennati et al. |

FOREIGN PATENT DOCUMENTS

| | | |
|---|---|---|
| DE | 30 17 168 | 11/1981 |
| DE | 100 35 415 | 1/2002 |
| EP | 0 298 441 | 1/1989 |
| EP | 0 309 085 | 3/1989 |
| EP | 0 266 434 | 10/1995 |
| EP | 1 092 386 | 4/2001 |
| GB | 2 033 575 | 5/1980 |
| GB | 2 055 206 | 2/1981 |
| GB | 1 599 241 | 9/1981 |
| GB | 2 111 864 | 1/1983 |
| JP | 62-83649 | 4/1987 |
| JP | 9-201337 | 8/1997 |
| JP | 2000-162176 | 6/2000 |
| RU | 2 069 863 | 11/1996 |
| RU | 2 073 242 | 2/1997 |
| RU | 2 088 927 | 8/1997 |
| SU | 1698724 | 12/1991 |
| WO | 85/04481 | 10/1985 |
| WO | 93/18395 | 9/1993 |
| WO | 93/18402 | 9/1993 |
| WO | 95/04496 | 2/1995 |
| WO | 97/39341 | 10/1997 |
| WO | 98/04190 | 2/1998 |
| WO | 98/09566 | 3/1998 |
| WO | 99/39627 | 8/1999 |
| WO | 99/44495 | 9/1999 |
| WO | 00/09996 | 2/2000 |
| WO | 00/43759 | 7/2000 |
| WO | 01/36952 | 5/2001 |
| WO | 01/47415 | 7/2001 |
| WO | 02/062214 | 8/2001 |
| WO | 02/069791 | 9/2002 |
| WO | 02/073179 | 9/2002 |
| WO | 03/017834 | 3/2003 |
| WO | 2004/021877 | 3/2004 |

OTHER PUBLICATIONS

English Abstract of DE 100 35 415 dated Jan. 31, 2002.
English Abstract of EP 1 092 386 dated Apr. 18, 2001.
Patent Abstracts of Japan of JP 9-201337 dated Aug. 5, 1997.
Patent Abstracts of Japan of JP 2000-162176 dated Jun. 16, 2000.
Patent Abstracts of Japan of JP 62-83649 dated Apr. 17, 1987.
Derwent Abstract of RU 2 069 863 dated Nov. 27, 1996.
English Abstract of RU 2 073 242 dated Feb. 10, 1997.
English Abstract of RU 2 088 927 dated Aug. 27, 1997.
Derwent Abstract of SU 1698724 dated Dec. 15, 1991.
Khalil, O. S. "Non-Invasive Glucose Measurement Technologies: An Update from 1999 to the Dawn of the New Millennium" *Diabetes Technology & Therapeutics* (2002) vol. 6, No. 5, pp. 660-695.
Choleau, C. et al. "Preventing of Hypoglycemia Using Risk Assessment With a Continuous Glucose Monitoring System" *Diabetes* (2002) vol. 51, pp. 3263-3273.
Feldman, Y. "Time Domain Dielectric Spectroscopy: An Advanced Measuring System" *Rev. Sci. Instrum.* (1996) vol. 67, No. 9, pp. 3208-3216.
Feldman, Y. D. et al. "Time Domain Dielectric Spectroscopy. A New Effective Tool for Physical Chemistry Investigation" *Colloid & Polymer Science* (1992) vol. 270, No. 8, pp. 768-780.
General Linear Least Squares in "Numerical Recipes in C: The Art of Scientific Computing" *Cambridge University Press. Programs* (1988) Chapter 15, pp. 671-681.

* cited by examiner

METHOD AND A DEVICE FOR MEASURING GLUCOSE

This is a continuation of International Application PCT/IB2002/003604 filed on Sep. 4, 2002, which designated the U.S., claims the benefit thereof and incorporates the same by reference.

TECHNICAL FIELD

The invention relates to a method and a device for measuring glucose in a sample, in particular in a sample of living body tissue.

BACKGROUND ART

Various non-invasive methods for measuring glucose in body tissue have been known. In particular, U.S. Pat. No. 5,792,668 by Fuller et al. describes a device where a square wave signal or a plurality of sine waves with differing frequencies are fed to a first electrode applied to the tissue. A second electrode is used for measuring a signal transmitted through the tissue. The phase and/or amplitude of the transmitted signal are used for determining the glucose level.

DISCLOSURE OF THE INVENTION

Hence, it is a general object of the invention to provide a method and a device for the non-invasive measurement of glucose.

This object is met by the independent claims. Accordingly, an end of a probe is applied to the sample. A pulse generator is used to generate single pulses to be fed into the probe. The pulses are reflected at the end of the probe, which acts as a fringing capacitor with field lines extending into the specimen, and the reflected pulses are measured by a reflection measuring device. An analyzer is used for determining at least one parameter of the reflected pulses and for determining the glucose level from this parameter or these parameters, e.g. by using calibration data stored in a memory.

In this context, the term "pulse" is understood to encompass not only isolated pulses having a rising and a trailing edge, but also pulses consisting of a rising or a trailing edge only, i.e. isolated transitions of the voltage level applied to the probe.

BRIEF DESCRIPTION OF THE DRAWINGS

The invention will be better understood and objects other than those set forth above will become apparent when consideration is given to the following detailed description thereof. Such description makes reference to the annexed drawings, wherein.

MODES FOR CARRYING OUT THE INVENTION

The preferred embodiment of the present invention is based on Time Domain Spectroscopy, where a pulse if fed to a probe, and end of which is applied to a sample, and where the time resolved characteristics of the reflected pulse are analyzed. For an overview and description of the theory of this method, see:

Y. D. Feldman et al., "Time domain dielectric spectroscopy. A new effective tool for physical chemistry investigation", Colloid & Polymer Science, Vol. 270, pp. 768—780 (1992), in the following called Ref. 1, and Y. D. Feldman et al., "Time domain dielectric spectroscopy. An advanced measuring system", Rev. Sci. Instrum. Vol. 67 (9), pp. 3208—3216 (1996), in the following called Ref. 2.

The disclosure of Ref. 2 is being incorporated herein by reference.

Figure 1:
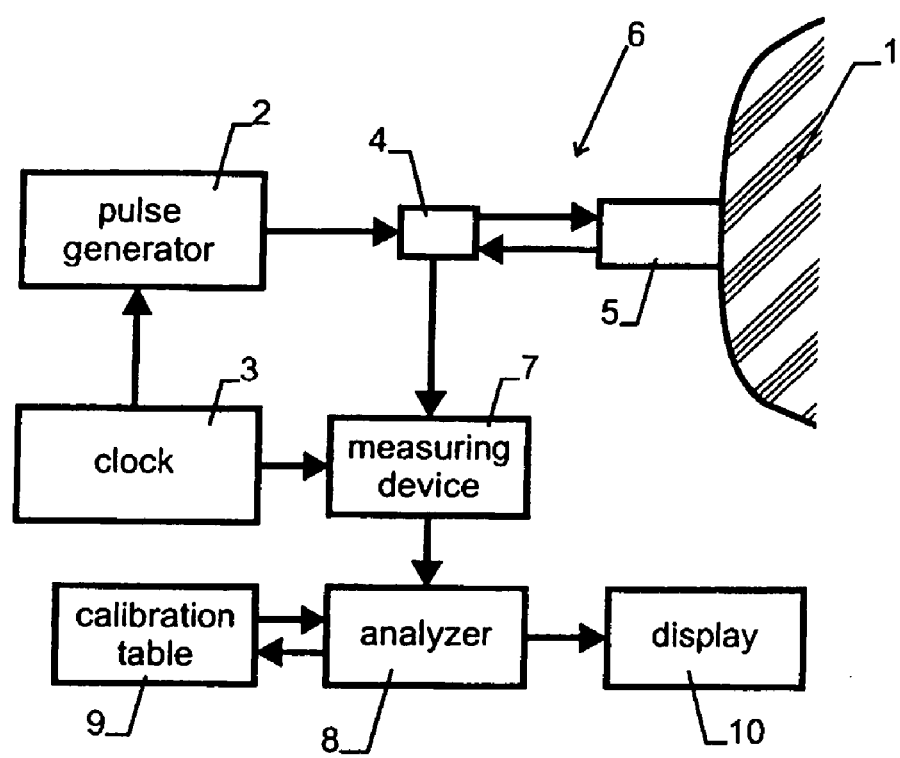
FIG. 1 is a block diagram of and embodiment of the invention.

An embodiment of a device for measuring the glucose concentration in a sample 1, in particular in the living human body, is shown in FIG. 1. It comprises a pulse generator 2 repetitively triggered by a clock 3 and generating pulses consisting of voltage transitions having a rise or fall time of less than 1 ns. The pulses are fed to a node 4 and from there to a probe 5, and end 6 of which is applied to sample 1. In a preferred embodiment of the invention, end 6 of the sample is applied to the skin of a subject.

Pulses reflected from end 6 arrive back at node 4 and are fed to a measuring device 7. In the present embodiment, measuring device 7 records the reflected pulses in time resolved manner.

The data from measuring device 7 are digitized and fed to an analyzer 8, such as a computer system, where they are processed. Using calibration data stored in a calibration table 9, analyzer 8 converts the data to a glucose level, which is e.g. displayed on a display 10.

Figure 2:
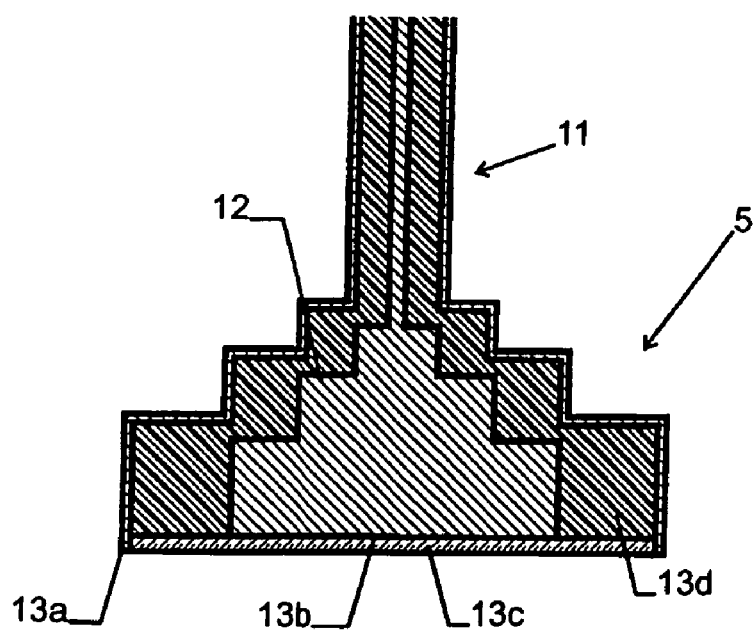
FIG. 2 is a sectional view of a first embodiment of a probe.

A first embodiment of a probe 5 of Chebishev-type symmetry as described in Ref. 2 is shown in FIG. 2. It comprises a coaxial transmission line 11 connected through a flaring section 12 to an annular electrode 13a and a circular central electrode 13b, wherein flaring section 12 provides impedance matching between transmission line 11 and electrodes 13a, 13b. Central electrode 13b may be covered by an anticorrosion coating 13c. A teflon layer 13d is arranged between the electrodes.

Figure 3:
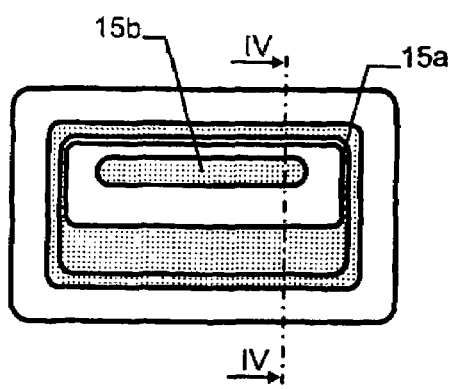
FIG. 3 is a view of a second embodiment of a probe as seen from the electrode side.
Figure 4:
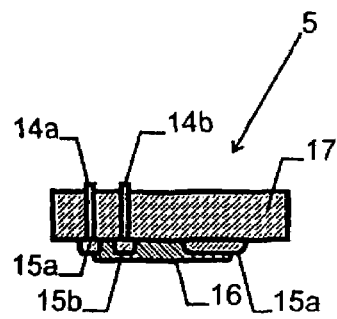
FIG. 4 is a section along line IV—IV of FIG. 3, FIG. 5 are sample traces of reflected pulses, FIG. 6 are calculated charges for the traces of FIG. 5, FIG. 7 are charges for two different glucose levels, FIG. 8 are charges at 19 ns measured for a subject during an extended time period with an oral glucose intake at t=26 min.

A second embodiment of a probe 5 is shown in FIGS. 3 and 4. Here, the signal is fed through terminals 14a, 14b to a an annular electrode 15a and a central strip electrode 15b, wherein the latter or both may be covered by a dielectric coating 16 and are mounted on a dielectric substrate 17. Central strip electrode 15b is not exactly centered within annular electrode 15a but offset in a first direction. Annular electrode 15a is thicker at a side remote from central strip electrode 15b and partially covered by dielectric coating 16 at this side.

Figure 5:
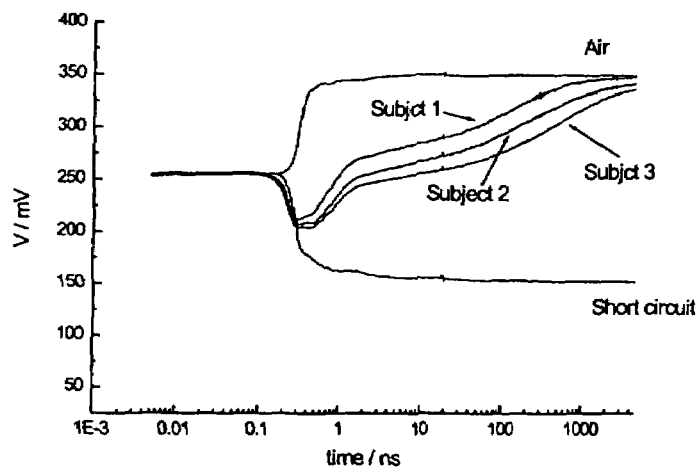

FIG. 5 shows typical signal traces of reflected pulses from the probe of FIG. 2 as a response to a pulse consisting of a single voltage transition of a rise time much smaller than 0.1 ns. The probe was applied to air or to three different subjects or it was short circuited at its electrode end.

As described in Ref. 1, an integration of the voltage traces of FIG. 5 allows to calculate a charge Q(t) accumulated on the capacitor formed by the electrodes. The corresponding curves for the three subjects of FIG. 5 are shown in FIG. 6.

Figure 6:
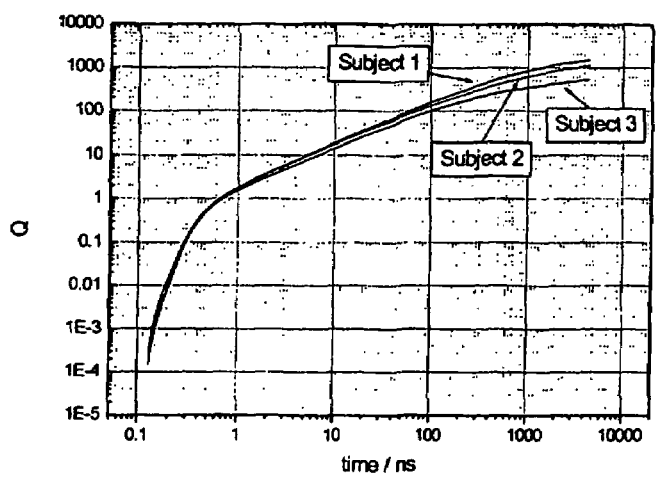
Figure 7:
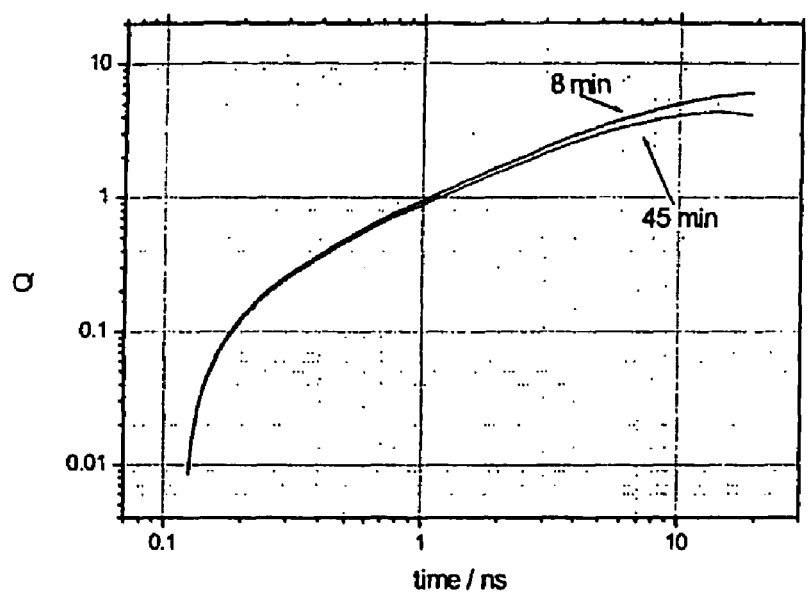

Experiments show that the traces of FIGS. 5 and 6 change when the glucose level in the tissues of the subjects vary. This is illustrated in FIG. 7 showing two charge traces measured with the probe of FIGS. 3 and 4. A first trace (at 8 min) was recorded before an oral glucose intake and one afterwards (at 45 min). The curves show a clear difference at 10 ns and later. It has been found that the effect is pronounced at larger times, but 1 µS is considered to be an upper limit for measurements due to an increasingly strong influence from other relaxation processes.

Hence, in a preferred embodiment, measuring device 7 is designed for carrying out at least one, preferably more than one, measurement in the range of 10 to 1000 ns after the generation of the pulse.

The duration of a pulse is preferably at least 10 ns since the relevant polarization processes were found to set in at this time scale.

Figure 8:
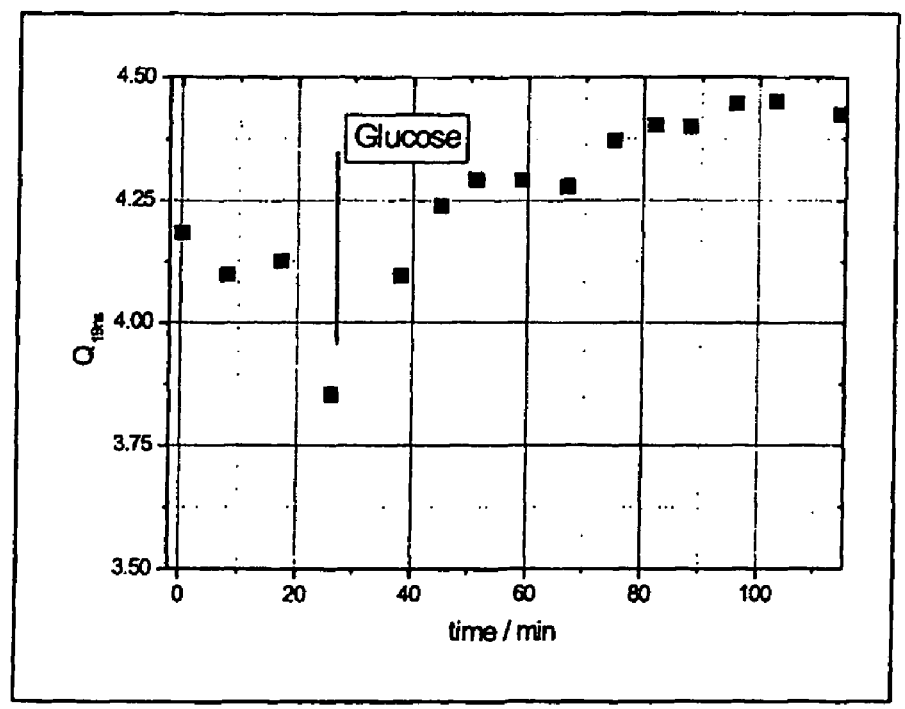

FIG. 8 shows the accumulated charge after 19 ns for a subject during a period of 100 min with oral glucose intake at t=26 min.

When ignoring the measured point at t=26 min (considered to be an outlier due to a sudden movement of the subject while drinking the glucose solution), the points show a clear increase of the charge after approximately 40 min when the glucose level in the subject's tissue starts to increase.

By running a calibration measurement where Q(t=19 ns) as shown in FIG. 8 and a reference glucose concentration determined conventionally are measured, calibration data can be obtained that allows to determine the glucose level from the charge Q(t=19 ns). This calibration data can be stored in calibration table 9 for being used to translate the measured charge to a glucose level.

For this purpose, the conventionally obtained glucose level $c_{gl}$ and the charge Q measured in the calibration measurement can e.g. be fitted to a function f using one or more parameters p1, p2, . . . , i.e. $c_{gl}$=f(Q, p1, p2 . . . ). The parameters p1, p2 . . . can be stored in calibration table 9, such that, during a later measurement, f(Q, p1, p2 . . . ) can be calculated for any value Q. The function f(Q) can e.g. be a straight line (i.e. f(Q, p1, p2)=p1 +Q·p2) or any other function that is found empirically or theoretically.

In the examples shown so far, measuring device 7 carries out a time resolved measurement of the reflected pulses. This data is digitized and integrated in analyzer 8 as described in Ref. 2 for calculating the charge Q(t) at t=19 ns. In another embodiment, the integration could also be carried out by analog circuitry before converting the charge Q(t=19 ns) to a digital value.

Also, the integration could be started at a time later than t=0 because the period up to t=1 ns shows only a very weak dependence on the glucose level (see FIG. 7). For a strong signal, the integration should, however, start not later than 1 ns after the start of the pulse.

The parameter measured by measuring device 7 is the voltage V(t) applied to probe 5, which includes a contribution of the reflected pulse. It is the sum of the input voltage V0(t) and the reflected voltage R(t). Instead of integrating the voltage V(t) as shown in Ref. 2, it is also possible to use V(t=19 ns) directly or to use another characteristic value derived from V(t), for example:

The current IQ through probe 5 can be calculated as shown in Ref. 2 and its value after e.g. 19 ns can be used.

The dielectric property $\epsilon^*(\omega)$ calculated from Eqn. (14) –(17) of Ref. 2 at a frequency $\omega$ of approximately 50 MHz can be used.

The difference of two voltages V(t) at different predefined times t1 and t2 or a slope of the voltage V(t) at a given time can be used.

While there are shown and described presently preferred embodiments of the invention, it is to be distinctly understood that the invention is not limited thereto but may be otherwise variously embodied and practiced within the scope of the following claims.

The invention claimed is:

1. A device for measuring a glucose level in a sample comprising
    a probe having an end to be applied to the sample,
    a pulse generator for generating electric pulses in the probe,
    a measuring device for measuring pulses reflected from the end of the probe, and
    an analyzer for determining at least one parameter of the reflected pulses measured by the measuring device and for determining the glucose level from said parameter, wherein the parameter is an integral over a period of time of a voltage including the reflected pulse, and in particular wherein the period of time ends less than 100 ns after generating the corresponding pulse in the pulse generator.

2. The device of claim 1, having a memory for storing calibration data for transforming the at least one parameter to the glucose level.

3. The device of claim 1, wherein the reflection measuring device carries out a time resolved measurement of the reflected pulses.

4. The device of claim 1, wherein the reflection measuring device carries out at least one measurement in a period of 10 to 1000 ns after generating a pulse in the pulse generator.

5. The device of claim 1, wherein the pulses generated by the pulse generator have rise and/or fall times of less than 1 ns, and a duration of at least 10 ns.

6. The device of claim 1 wherein the integral starts less than 1 ns after generating the corresponding pulse in the pulse generator, and in particular wherein the integral starts when generating the corresponding pulse in the pulse generator.

7. A device for measuring a glucose level in a sample comprising
    a probe having an end to be applied to the sample,
    a pulse generator for generating electric pulses in the probe,
    a measuring device for measuring pulses reflected from the end of the probe, and
    an analyzer for determining at least one parameter of the reflected pulses measured by the measuring device and for determining the glucose level from said parameter, wherein the parameter is a difference of two voltages including the reflected pulse measured at different times after generating the corresponding pulse in the pulse generator.

8. A device for measuring a glucose level in a sample comprising
    a probe having an end to be applied to the sample,
    a pulse generator for generating electric pulses in the probe,
    a measuring device for measuring pulses reflected from the end of the probe, and
    an analyzer for determining at least one parameter of the reflected pulses measured by the measuring device and for determining the glucose level from said parameter, wherein the parameter is a slope of a voltage curve including the reflected pulse measured at a given time after generating the corresponding pulse in the pulse generator.

* * * * *